United States Patent [19]

Bauman

[11] Patent Number: 4,596,239

[45] Date of Patent: Jun. 24, 1986

[54] LIGHT SOURCE FOR ILLUMINATING AND EXAMINING DEVICES

[75] Inventor: Jack Bauman, Pacific Palisades, Calif.

[73] Assignee: General Medical Products, Inc., Santa Monica, Calif.

[21] Appl. No.: 721,562

[22] Filed: Apr. 10, 1985

[51] Int. Cl.$^4$ .............................................. A61B 1/06
[52] U.S. Cl. ....................................... 128/11; 362/204
[58] Field of Search ..................... 128/11, 6; 362/205, 362/208, 157, 204

[56] References Cited

U.S. PATENT DOCUMENTS

| | | | |
|---|---|---|---|
| 4,273,112 | 6/1981 | Heine et al. | 128/11 |
| 4,406,280 | 9/1983 | Upsher | 128/11 |
| 4,495,551 | 1/1985 | Foltz | 362/204 |
| 4,556,052 | 12/1985 | Muller | 128/11 |

Primary Examiner—William H. Grieb
Attorney, Agent, or Firm—Fulwider, Patton, Rieber, Lee & Utecht

[57] ABSTRACT

This invention is directed to an improved light source for illuminating examining devices, particularly medical devices such as laryngoscopes. The light source comprises an electrically conducting light bulb holder with a longitudinal passageway therethrough, a light bulb with two depending electrodes snugly positioned in one end of the passageway with a portion of the light generation means extending out of the passageway, a non-conducting insert also having a longitudinal passageway telescopicly interfitting into the other end of the passageway and urging one of the electrodes disposed between the insert and the bulb holder into electrical contact with the latter and an electrically conducting rivet or plug snugly interfitting the exposed longitudinal end of the passage was in the insert and electrically contacting the second electrode disposed within said insert passageway and forming a terminal for the light source. The light source preferably fits into a cavity of a support frame having a metallized, electrically conductive surface. The frame, which holds the batteries and forms the switch to energize the light source position within the cavity, is disposed in the handle of an illuminating or examining device such as a laryngoscope.

13 Claims, 5 Drawing Figures

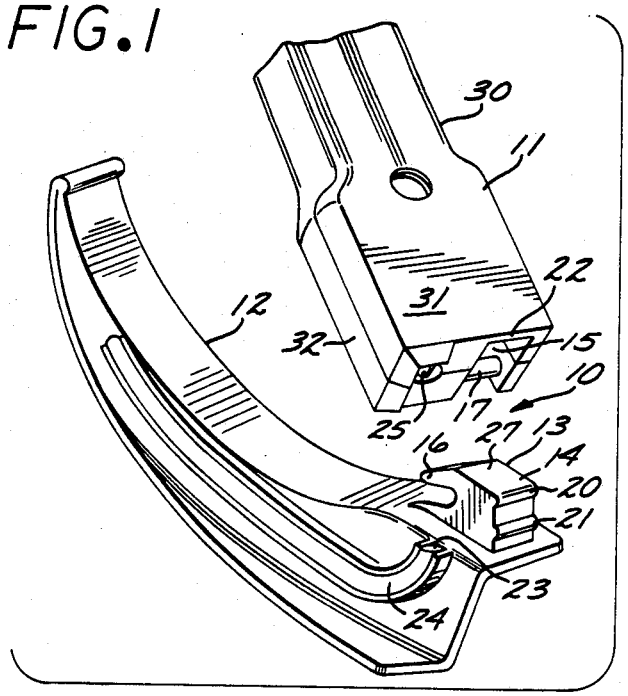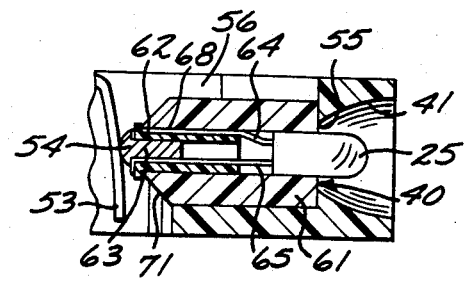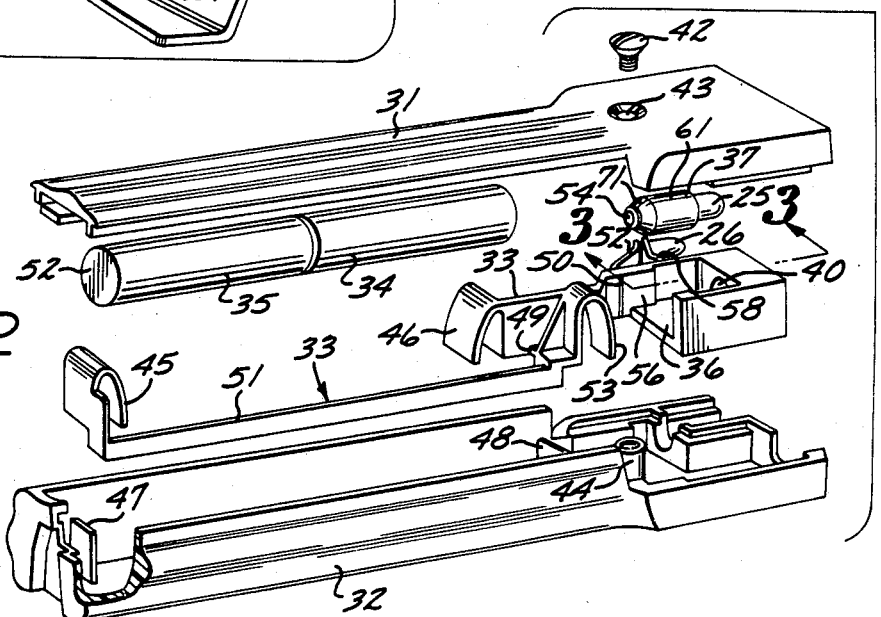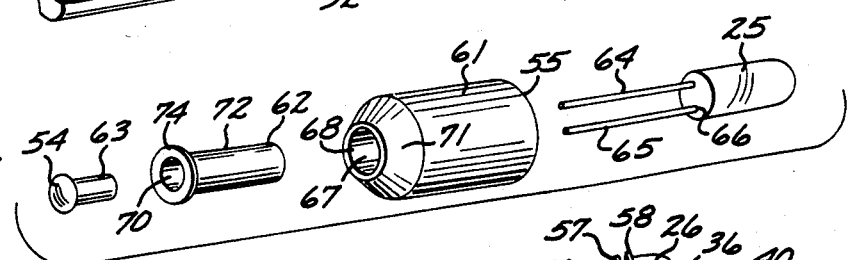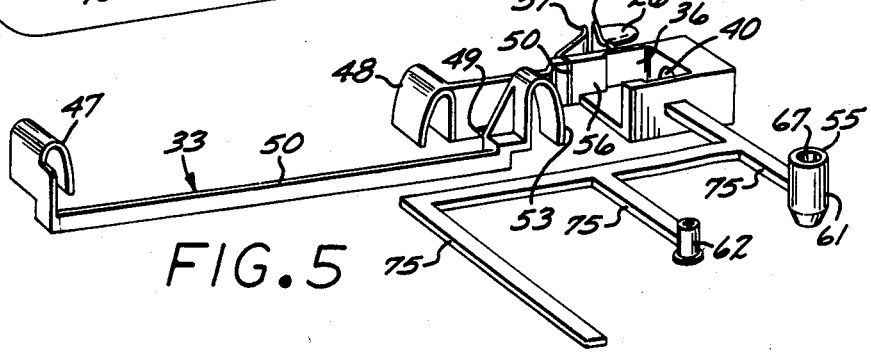

LIGHT SOURCE FOR ILLUMINATING AND EXAMINING DEVICES

BACKGROUND OF THE INVENTION

This invention relates to an improved light source for illuminating and examining devices such as laryngoscopes.

Laryngoscopes generally comprise a detachable blade and a cooperating handle which are connected together in an L-shaped configuration. The handle serves as an enclosure for one or more batteries which energize a light source in the top of the handle. The switch for energizing the light source is usually positioned at the top of the handle immediately adjacent to the light source and is activated by the blade when it is connected to the handle into an operative position. Light from the light source is directed to the light receiving face at the proximal end of the light conductor disposed in or on the blade. Light passes through the light conductor to the distal end thereof to illuminate the field of view such as a patient's mouth and larynx during the examination thereof by medical personnel. Although the instrument is useful in examining the larynx, the primary function of a laryngoscope is to expose the larynx in order to facilitate the insertion of an endoptracheal tube into the trachea of the lungs to administer anesthetic gases therein.

With the prior metallic laryngoscopes, the electrical connections and assembly of the light source, the switch and the battery pack involved extensive manual labor, but the labor costs were relatively insignificant in comparsion with the costs of the metal handle casing and the metal blade. However, with the advent of disposable plastic blades and plastic handles, the costs for manual assembly for the handle components became extremely high in comparison with other manufacturing and material costs.

The development of a metal coated plastic support frame described and claimed in copending application Ser. No. 669,473, filed Nov. 8, 1984, by the present inventor was a substantial advance in the art inasmuch as the battery holder, the switch and the light components could be produced with a single unit of metalized plastic which is formed by injection molding of a suitable plastic material such as acrylonitrile-butadiene-styrene polymers (ABS).

While the metallized plastic support frame described in the aforesaid patent application was a substantial advance, the manufacture and assembly of the light source still involved much manual labor and relatively high labor costs. The present invention, which provides a relatively cheap and simple to manufacture light source, was developed to satisfy the needs for simplifying the assembly and lowering the cost of the light source for illuminating and/or examining devices such as laryngoscopes.

SUMMARY OF THE INVENTION

The present invention provides a simple and low cost light source for illuminating and examining devices such as laryngoscopes and particularly to a light source which can be, for the most part, produced with a metal coated support frame such as described in the claims in copending application Ser. No. 669,473, filed Nov. 8, 1984, by the present inventor which is hereby incorporated in its entirety.

The light source in accordance with the invention comprises a high intensity light bulb such as a Krypton light bulb which has two depending electrodes for electrical connection to a power source and to a switch. An electrically conducting light bulb holder is provided with a central longitudinal passageway which is adapted to receive and hold the light bulb with the depending electrodes contained within the passageway therein. The holder, preferably cylindrically shaped, is formed from metallic materials or plastic materials with a metalized coating so that effective electrical conduction can be maintained. A significant portion of the Krypton bulb extends out of one end of the light holder.

The light source is also provided with an insert adapted to be pushed into and snugly interfit with the opposite end of the passageway in the light bulb holder, with one depending electrode from the light bulb engaged between the outer surface of the insert and the inner conducting surface of the passageway through the light bulb holder. The insert is also provided with a longitudinal passageway but it has an essentially non-conductive surface and it is adapted to receive the other depending electrode from the light bulb to thereby maintain electrical separation between the two depending electrodes.

One end of the insert telescopically interfits with the passageway of the light bulb holder and the free end of the insert is provided with an opening adapted to receive an electrically conducting element which contacts the second electrode within the longitudinal passageway thereof and which extends beyond the outer end of the insert to thereby function as an electrical contact element for the light source. The metal or metalized plastic light bulb holder when installed in the cavity provided is electrically connected usually to the metallic or metallized walls thereof which are in electrical connection with one terminal of a light switch. The switch has one other terminal which is electrically connected to the opposing terminal of the power source, usually a battery pack.

The light bulb holder and the insert are preferably formed with the internal support frame which includes the battery holder and the switch in accordance with the inventor's previously mentioned copending application. Th plastic elements of the light source can be removed from the runners by hand and assembled easily and quickly. Preferably, the light bulb holder is metal plated along with the support frame, but the small non-conducting insert is removed from the runner prior to coating with metal. However, it should be recognized that for purposes of operability only the central passageway contacting one electrode or the outer surface contacting the other electrode needs to be non-conducting.

To assemble the light source the krypton high intensity light bulb is pushed into one end of the light bulb holder with the two depending electrodes of the light bulb located within the passageway thereof. The non-conducting insert is pressed into the passageway at the opposite end of the light bulb holder with one of the electrodes positioned between the outer surface of the insert and the conducting wall of the passageway. The fit between the two elements is tight enough so that the electrode is pressed into electrical contact with the said conducting wall. The other depending electrode is contained within the longitudinal passageway of the non-conducting insert. An electrically conducting element such as a metal rivet is pushed into the opening of the passageway within the non-conducting insert to be electrically connected to the second electrode of the light bulb contained therein. The electrically conducting element extends outwardly from the end of the insert to act as an electrical contact for the light source.

The individual components of the light source of the invention are very simply and inexpensively manufactured and they can be assembled reliably and quickly by unskilled labor. These and other advantages of the invention will become more apparent in the following detailed description of the invention when taken in conjunction with the accompanying drawings.

BRIEF DESCRIPTION OF THE DRAWINGS

FIG. 1 is an exploded in perspective view of the blade and handle of the laryngoscope;

FIG. 2 is an exploded view in perspective illustrating the laryngoscope handle shown in FIG. 1 with a unitary support frame adapted to be secured in the handle:

FIG. 3 is a side view of a light source, partially in section, taken along the lines 3—3 shown in FIG. 2;

FIG. 4 is an expanded, perspective view of the light source shown in FIG. 3 illustrating the assembly thereof; and FIG. 5 is a perspective view of the support frame shown in FIG. 2 as manufactured with parts attached.

In the drawings all corresponding parts are numbered the same.

DETAILED DESCRIPTION OF THE INVENTION

With reference to FIG. 1 a laryngoscope 10 generally comprises a handle 11, a detachable blade 12 and means 13 to detachably secure the blade 12 to handle 11 in a generally L-shaped configuration. The instrument is utilized to depress a patient's tongue and mandible to expose the patient's larynx during an examination thereof or the insertion of an endotracheal tube.

The blade 12 is attached to the handle 11 in a pivotal fashion by means 13 which includes an appendage 14. The appendage 14 is inserted into the open top channel 15 of the handle 11 with a pivotal motion so that the front end 16 of appendage 14 is hooked underneath the pivot rod 17 provided in the channel 15. Detents 20 and 21 are provided on appendage 14 to engage a groove (not shown) in the back wall 22 of the channel 15 to urge the appendage 14 into a more firm engagement with pivot rod 17 and to thereby fix the blade 12 with respect to the handle 11 in a generally L-shaped configuration so that light receiving face 23 of the light conductor 24 is in a light receiving position adjacent to light bulb 25. Light switch 26 (shown in FIG. 2) is actuated by the bottom face 27 of appendage 14 when the blade 12 is in the operative position.

With particular reference to FIG. 2, the handle 11 includes a shell or housing 30 comprising a top section 31 and a bottom section 32. A unitary support frame 33 is secured within the shell 30 and is adapted to support batteries 34 and 35. The support frame 33 is provided with a cavity 36 which is adapted to receive light source 37 which includes bulb 25 which passes through aperture 40 which leads into the reflector 41. Shell 30 is formed by joining sections 31 and 32 by means of a screw 42 which passes through the opening 43 in section 31 and which is threadably secured to the upstanding post 44 fixed to the interior of section 32.

Unitary support frame 33 is secured within the shell 30 by the back sides of electrical contact elements 45 and 46 thereof which snugly interfit with upstanding wall 47 and 48 respectively.

The support frame 33 is provided with a metal coating to conduct electricity between the batteries 34 and 35, light switch 26 and light bulb 25 with discontinuities 45 and 46 in the metallic coating to control the flow of electrical current therebetween. Preferably, the surface of support frame 33 is provided with an electrically conducting coating such as copper, aluminum, silver or tin and then followed with a reflective coating of aluminum, silver or nickel or chromium to ensure a reflective surface on reflector 41. Discontinuity 45 electrically segregates the battery holder 50 from other sections of support frame 33. Control element 47 electrically connects the negative terminal 52 of battery 35 with contact element 53 which electically contacts terminal 54 of light source 37. The spring action of contact element 53 urges the light source 37 forward until shoulder 55 thereof contacts wall 56 of cavity 36 to properly position the light within the reflector 41 for optimum light transmission to the light conductor face 23.

Discontinuity 46 electrically separates the contact elements 57 and 58 of light switch 26 so that the positive terminal of battery 34, which is in contact with contact element 48, is not in electrical communication with the light source 37 until the elements 57 and 58 are brought into contact when the blade is mounted on the handle.

Reference is made to FIGS. 3 and 4 which illustrate light source 37 embodying features of the invention which comprises a light bulb 25, preferably of high intensity, electrically conducting bulb holder 61, insert 62 and a rivet 63. The high intensity bulb 25 shown is provided with electrodes 64 and 65 which depend from the lower end 66 thereof and which extend into the longitudinal passageway 67 of conductive bulb holder 61. The lower end 66 of light bulb 25 snugly fits into the passageway 67. The top end 70 of light bulb 25 extends out from the bulb holder 61 a distance which ensures proper positioning within the reflector 41 when the light source 37 is mounted within cavity 36 in frame 33. An essentially non-conducting insert 62 having a longitudinal passageway 70 is pushed into the tapered end 71 of bulb holder 61 with electrode 64 positioned between the outer wall 72 of insert 62 and inner conductive surface 73 of passageway 67 so as to be in electrical contact therewith. Electrode 65 is maintained within the non-conducting passageway 70 of insert 62.

Electrically conducting rivet or plug 63 is fitted into the open end of insert 62 to electrically contact the depending electrode 65 in passageway 70. The rivet or plug 63 extends outwardly from the open end 74 of insert 62 to act as an electrical terminal 54 for the light source 37 which is urged against contact element 53. FIG. 5 illustrates a mode of assembly of the component parts of the light source 36. As is evident, no skills and no tools are needed for the assembly. The components are merely pushed together.

FIG. 5 is a perspective view of the unitary support frame assembly 33 as it is preferably manufactured. It is essentially the same view as that shown in FIG. 3 except that the plastic material 75 which solidifies in the runners, which feed uncured plastic to the die form frame 33, remains attached to the frame 33. The bulb holder 61 and the insert 62 which are molded simultaneously with frame 33 also remain fixed to the material 75 as manufactured. The insert 62 which is non-conductive is removed before the molded assembly is metal plated. The bulb holder 61 is usually left attached until the light source 36 is to be assembled. Although not shown in the drawings, rivit or plug 63 can also be manufactured simultaneously as with bulb holder 61 and insert 62.

The support frame 33 and the bulb holder 61 and the insert 62 molded simultaneously therewith are preferably formed from a platable grade of ABS such as that sold under the trade name "Cyculac" by the Borg-Warner Company and the entire assembly is very efficiently and effectively formed by injection molding.

The support frame 33 and attached parts 61 and 62 can be readily plated by first non-electrically plating a thin copper layer of about 0.01–0.1 mils (0.25–2.5 microns) thick and then electrolyticly plating another copper layer to form a conductive layer of about 0.5 to 2 mils (12.5–50 microns) thick. A thin reflective layer of aluminum about 0.01 to 0.1 mils (0.25–2.5 microns) thick is subsequently applied to the copper coating, preferably by vacuum deposition to form a reflective surface and to provide corrosion protection. Other conductive and reflective coatings of the same approximate thickness can also be utilized as previously discussed. A much better bond can be obtained between the ABS substrate and the initial electroless copper strike if the ABS substrate is first etches in acid to roughen the surface thereof.

If the discontinuities 45 and 46 separating the various electrically conductive areas of the frame 33 are not made during the plating processes they are mechanically formed before the frame is installed in the illuminating or examining device by removing strips of the electrically conducting metallic layer.

By manufacturing the light source parts with the support frame in accordance with the invention, the manufacturing costs of the light source can be substantially reduced. The light source 36 is assembled and inserted into the cavity 36 of frame 33. The assembly is simple and very quickly accomplished. There is no need for a high level of mechanical skills or manual dexterity in the assembly and for the most part no tools are needed. Moreover, because of its simplicity, the reliability and durability of the product is excellent.

While the specific embodiment described herein has been limited to a light source for use in laryngoscopes, the invention can be applied to a wide variety of illuminating or examining devices and other electrically conducting three dimensional instruments and devices. Moreover, modifications and improvements can be made to the invention without departing from the inventive concepts thereof.

I claim:

1. A light source for an illuminating or an examining device comprising:
   (a) a light bulb having a first and a second depending electrode means;
   (b) an electrically conductive light bulb holder having a longitudinal passageway therein which is adapted to receive and hold the light bulb at one end thereof and to contain the depending electrode means;
   (c) an electrically non-conductive insert which is adapted to be inserted into the end of the passageway of the bulb holder opposite to the end thereof holding the bulb, and to thereby urge the first depending electrode means disposed within the passageway of the bulb holder into electrical contact with the wall thereof and which has a longitudinal passageway therein which contains the second depending electrode means to thereby electrically separate the second depending electrode means from the first depending electrode means; and
   (d) an electrical conducting means which is in electrical contact with the second depending electrode means disposed within the passageway of the non-conducting insert and which extends beyond the exposed end of the non-conducting insert to thereby form an electrical contact for energizing the light bulb.

2. The light source of claim 1 wherein the bulb holder is a metal coated plastic part.

3. The light source of claim 2 wherein the bulb holder is formed from acrylonitril-butadiene-styrene polymers.

4. The light source of claim 1 wherein the electrically conducting means in electrical contact with the second depending electrode means in the passageway of the non-conducting insert is a metal rivet.

5. The light source of claim 1 wherein the light bulb is a high intensity light bulb having two wire electrodes depending therefrom.

6. The light source of claim 5 wherein the electrically non-conductive insert snugly fits into the passageway of the bulb holder so that the first wire electrode of the light bulb, which is positioned between the outside surface of the insert and the electrically conducting wall of the longitudinal passageway in the light bulb holder, is thereby urged into electrical contact with the electrically conducting passageway wall.

7. In an illuminating or examining device having an electrical power source, a light source and a switch to control the flow of electrical current energizing the light source, the improvement comprising a light source having:
   (a) a light bulb with two depending electrode means;
   (b) an electrically conductive light bulb holder having a longitudinal passageway therein which is adapted at one end thereof to receive and hold the light bulb and to contain the depending electrode means;
   (c) an electrically non-conductive insert which is adapted to be inserted into the end of the passageway of the bulb holder opposite to the end thereof holding the bulb and to thereby urge one of the depending electrode means into electrical contact with the wall thereof and which has a longitudinal passageway therein which contains the second depending electrode means to thereby electrically separate the second depending electrode means from the first depending electrode means; and
   (d) an electrical conducting means which is in electrical contact with the second depending electrode means disposed within the passageway of the non-conducting insert and which extends beyond the free end of the non-conducting insert to thereby form an electrical contact for energizing the light bulb.

8. The illuminating or examining device of claim 7 which is a laryngoscope comprising a handle having the electrical power source, light switch and light source and an elongated blade which is mounted to the handle in a generally L-shaped configuration.

9. The illuminating or examining device of claim 7 wherein the power source is a battery pack comprising one or more batteries.

10. An illuminating or examining device including:
    (a) a unitary support frame having a battery section adapted to hold one or more batteries, a light section having a light source and a reflector adapted to receive a light bulb from the light source, a light switch for controlling the flow of electrical current to energize the light bulb, means to secure the unitary support frame within the interior of a housing with the light bulb in optical communication with an opening provided therefor in the housing;

(b) electrical conducting means integral with the unitary support frame and in electrical contact with the battery, the light bulb and the light switch to pass electrical current therebetween when the light switch is activated; and (c) a light source comprising
  (i) a light bulb having a first and a second depending electrode means;
  (ii) an electrically conductive light bulb holder having a longitudinal passageway therein which is adapted to receive and hold the light bulb at one end thereof and to contain the depending electrode means;
  (iii) an electrically non-conductive insert which is adapted to be inserted into the end of the passageway of the bulb holder opposite to the end thereof holding the bulb, and to thereby urge first depending electrode means disposed within the passageway of the bulb holder into electrical contact with the wall thereof and which has a longitudinal passageway therein which contains the second depending electrode means to thereby electrically separate the second depending electrode means from the first depending electrode means; and
  (iv) an electrical conducting means which is in electrical contact with the second depending electrode means disposed within the passageway of the insert and which extends beyond the exposed end of the non-conducting insert to thereby form an electrical contact for energizing the light bulb.

11. The illuminating or examining device of claim 10 wherein the bulb holder of the light source is adapted to snap fit into a metal plated cavity in said unitary frame.

12. The illuminating or examining device of claim 11 wherein the metal plated cavity is provided with a passageway leading to the central area of the reflector and is adapted to receive the light bulb.

13. The illuminating or examining device of claim 12 wherein the diameter of the passageway leading to the reflector is large enough to allow the passage of the light bulb therethrough but smaller than the diameter of the light bulb holder so that the bulb holder is thereby held against the cavity wall and the bulb is properly positioned within the reflector.

* * * * *